(12) United States Patent
Alexander et al.

(10) Patent No.: US 7,489,968 B1
(45) Date of Patent: Feb. 10, 2009

(54) PRE-MOLDED HEADER WITH UNIVERSAL TIP-TO-TIP FEEDTHRU ADAPTOR

(75) Inventors: William Alexander, Castaic, CA (US); Christopher Fleck, Canyon Country, CA (US); Sergey Safarevich, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 398 days.

(21) Appl. No.: 11/399,993

(22) Filed: Apr. 7, 2006

(51) Int. Cl.
*A61N 1/375* (2006.01)

(52) U.S. Cl. .......................................... 607/36; 607/37

(58) Field of Classification Search ............... 607/9–34, 607/36, 37; 174/50.5–50.59; 439/909; 604/533; 429/180
See application file for complete search history.

(56) References Cited

U.S. PATENT DOCUMENTS

| | | | |
|---|---|---|---|
| 5,103,818 A | 4/1992 | Maston et al. ............ 128/419 P |
| 5,620,476 A | 4/1997 | Truex et al. .................... 607/36 |
| 5,679,026 A * | 10/1997 | Fain et al. .................... 439/651 |
| 5,851,221 A * | 12/1998 | Rieder et al. .................. 607/93 |
| 5,877,472 A | 3/1999 | Campbell et al. ...... 219/121.64 |
| 5,919,215 A * | 7/1999 | Wiklund et al. ............... 607/36 |
| 6,817,905 B2 * | 11/2004 | Zart et al. .................... 439/736 |
| 2002/0038136 A1 * | 3/2002 | Zaouali et al. ................ 607/36 |
| 2002/0107554 A1 * | 8/2002 | Biggs et al. .................... 607/37 |
| 2003/0040780 A1 * | 2/2003 | Haeg et al. .................... 607/36 |
| 2003/0045911 A1 | 3/2003 | Bruchmann et al. ........... 607/36 |
| 2004/0093038 A1 * | 5/2004 | Biggs et al. .................... 607/37 |
| 2004/0257884 A1 | 12/2004 | Dalton et al. ................ 365/199 |

FOREIGN PATENT DOCUMENTS

| | | |
|---|---|---|
| EP | 1 230 948 A2 | 8/2002 |
| EP | 1 230 949 A2 | 8/2002 |
| EP | 1 230 948 A3 | 8/2003 |
| EP | 1 230 949 A3 | 8/2003 |
| EP | 1 417 986 A1 | 5/2004 |

* cited by examiner

*Primary Examiner*—Mark W Bockelman
*Assistant Examiner*—Roland Dinga

(57) ABSTRACT

In fabricating a header assembly of an implantable medical device, one end of a bore contact wire attached to a connector block is keyed with one guiding channel at an upper region of a feedthru adapter and through the adapter to its undersurface. An opposite end is bent into conformance with an orientation channel on the adaptor undersurface. A tip end of a feedthru wire connected to electronic circuitry of the medical device and projecting out of a casing mounting surface is bent for alignment with the orientation channel so end portions of the feedthru wire and bore contact wire are in end to end engagement, then welded together. A plastic header is molded to encapsulate the adapter, connector block, and bore contact wire and, when solidified, has an undersurface for engagement on the casing and an elongated receptacle aligned with a connector block bore to receive the lead.

7 Claims, 12 Drawing Sheets

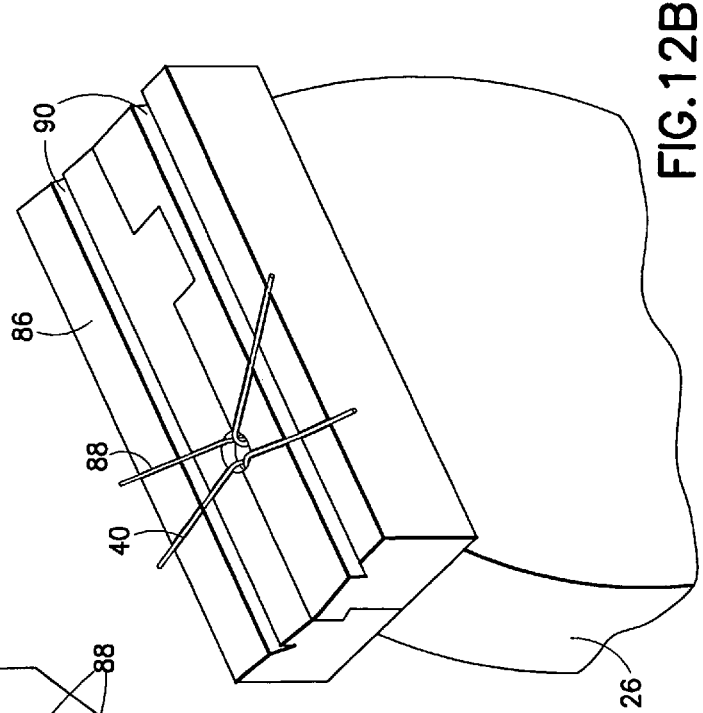
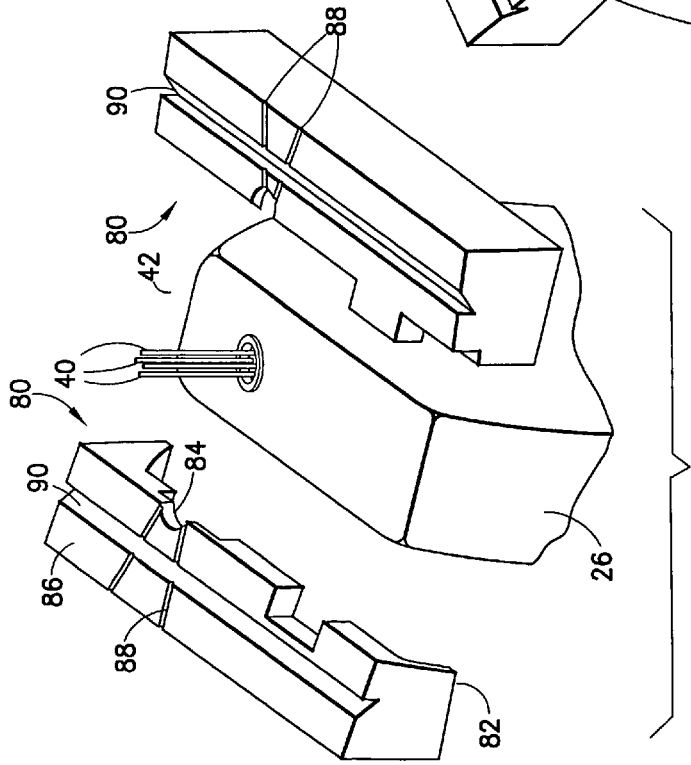
FIG. 12B
FIG. 12A

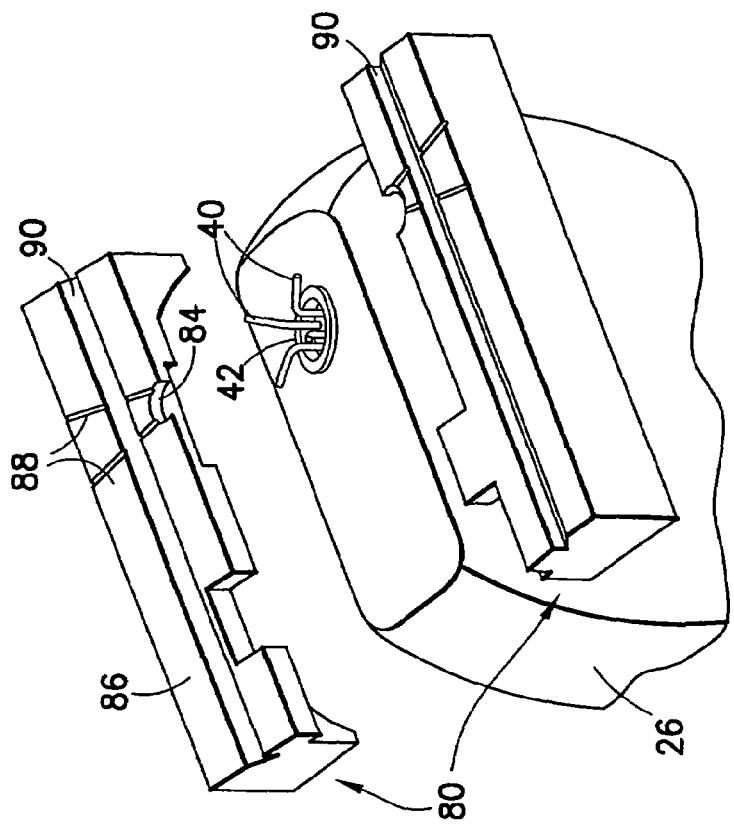
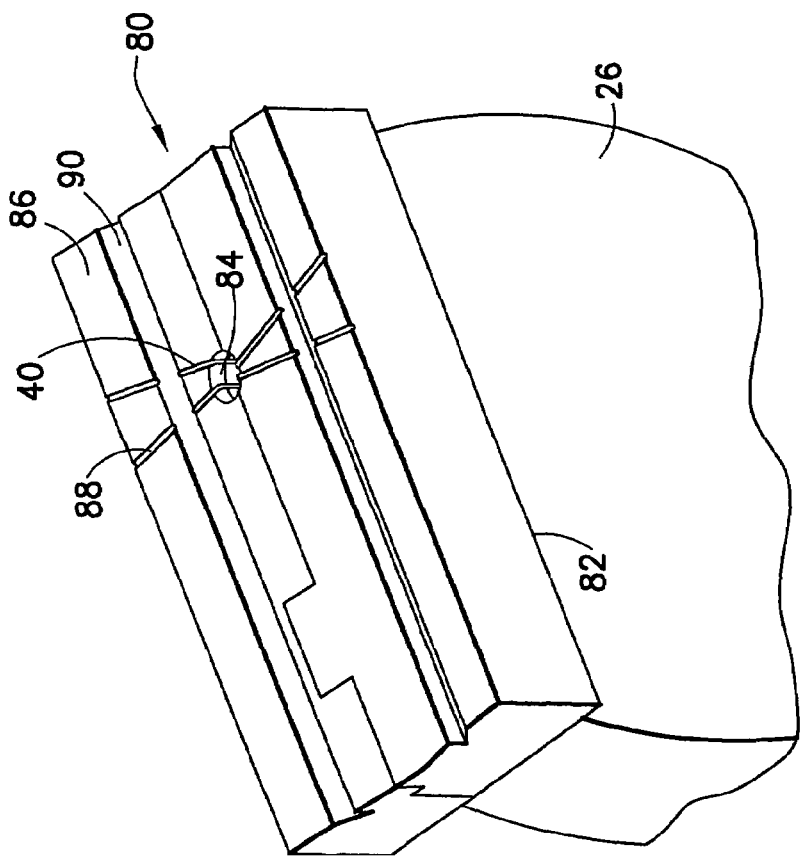
FIG. 12D
FIG. 12C

PRE-MOLDED HEADER WITH UNIVERSAL TIP-TO-TIP FEEDTHRU ADAPTOR

TECHNICAL FIELD

The present invention relates generally to an electrical header assembly forming part of an implantable medical device (IMD), such a header assembly having one or more electrical receptacles each adapted to receive an implantable lead and to connect the lead to electronic circuits within the IMD. More particularly, the invention relates to a pre-molded header assembly with components pre-assembled in a proper configuration, then encapsulated by plastic material during a casting process.

BACKGROUND

Cardiac stimulation systems commonly include a pulse generating device or pulse generator, such as a pacemaker or implantable cardioverter-defibrillator (ICD), that is electrically connected to the heart by at least one electrical lead. An electrical lead provides an electrical pathway between the pulse generator, connected to the proximal end of the lead, and myocardial tissue, in contact with the distal end of the lead. In such a manner, electrical pulses emitted by the pulse generator travel through the lead and stimulate the heart. Intrinsic cardiac signals may be sensed by electrodes located on the lead and conducted via the lead to sense amplifiers in the device for monitoring the heart's natural rhythm.

As implantable electrical devices have increased in their complexity, there have been an increasing variety of electrical lead systems developed for use in conjunction with these devices. Nowhere is this more apparent than in the context of ICDs, which may include two, three or more leads located for sensing or stimulating up to all four heart chambers. The leads themselves may carry one, two, three, or more electrodes, and may employ a variety of different electrical connector configurations and types. As a result, manufacturers of implantable pacemakers and ICDs have had to produce their products with a variety of connector block configurations, capable of use with different lead systems. However, there are standards which must be followed by manufacturers and the present invention is reflective of these standards.

The pulse generator is usually implanted in a subcutaneous cavity, and the leads extend either transvenously to the internal cavities of the heart, or to patch electrodes located on external surfaces of the heart.

The leads generally include at least one electrode located at a distal end and an electrical connector for interconnection to the pulse generator at the proximal end. The connector at the proximal end and the distal electrode are interconnected by at least one conductor extending through an insulated body. It is common, as already mentioned, for the leads to include two or more electrodes and two or more electrical contacts at the connector.

The connector is inserted into a receiving orifice in a header assembly of the pulse generator. The main body of the pulse generator is generally a metallic self-contained hermetically sealed housing or can which encloses the source of electrical energy and electronic circuitry for controlling the electrical stimulus delivered by the lead and isolates the electronic components from the body environment. The header assembly of the pulse generator defining the receiving orifice may be formed from a biocompatible plastic material which conventionally has been formed and bonded to the main body of the pulse generator. It is current practice to fabricate the header assembly of the plastic material, possibly employing the cast epoxy process. For the cast epoxy process, the liquid epoxy consists of two parts which need to be mixed together with very precise proportions. The cast epoxy process is labor intensive and time consuming and it frequently occurs that the epoxy leaks into the connector blocks, requiring its removal or substantial reworking of the assembly.

More recently, attempts have been made to provide preformed header assemblies and the present invention is an improvement of this preferred technique.

It was in light of the foregoing that the present invention was conceived and has now been reduced to practice.

SUMMARY

In fabricating a header assembly of an implantable medical device, one end of a bore contact wire attached to a connector block is keyed with one orientation channel on the top surface of a feedthru adapter and through the adapter to its undersurface. An opposite end is bent into conformance with another orientation channel on the adaptor undersurface. A tip end of a feedthru wire connected to electronic circuitry of the medical device and projecting out of a casing mounting surface is bent for alignment with the other orientation channel so end portions of the feedthru wire and bore contact wire are in end to end engagement, then welded together. A plastic header is molded to encapsulate the adapter, connector block, and bore contact wire and, when solidified, has an undersurface for engagement on the casing and an elongated receptacle aligned with a connector block bore to receive the lead.

The implantable medical device includes a sealed casing enclosing electronic circuitry and the feedthru wire from the electronic circuitry projects out of a mounting surface of the casing. The pre-formed header has an elongated receptacle and an undersurface for mounting engagement on the casing's mounting surface and includes the conductive connector block having a bore aligned with the receptacle for receiving a proximal end portion of a lead carrying an electrical terminal. Suitable anchors attach the header to the casing so that when the header assembly is engageably mounted on the casing with its undersurface contiguous with the mounting surface of the casing, the bore contact wire, in a manner to be described, conductively engages the feedthru wire from the casing.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

BRIEF DESCRIPTION OF THE DRAWINGS

The foregoing aspects and other features of the present invention are explained in the following description, taken in connection with the accompanying drawings, wherein:

FIG. 2A is a perspective view, similar to FIG. 2, but with some components thereof configured in a later stage of the construction of the medical device;

FIG. 3A is a side elevation view, similar to FIG. 3, but with some components thereof configured in a later stage of the construction of the medical device;

FIG. 3B is a top plan view of the casing of the medical device illustrated in FIG. 3A;

FIG. 7 is a bottom plan view of the header with certain portions being broken away to illustrate the interior thereof;

FIGS. 12A, 12B, 12C, and 12D are perspective views illustrating a series of operations performed on the casing of the medical device according to the invention;

DETAILED DESCRIPTION

Figure 1:
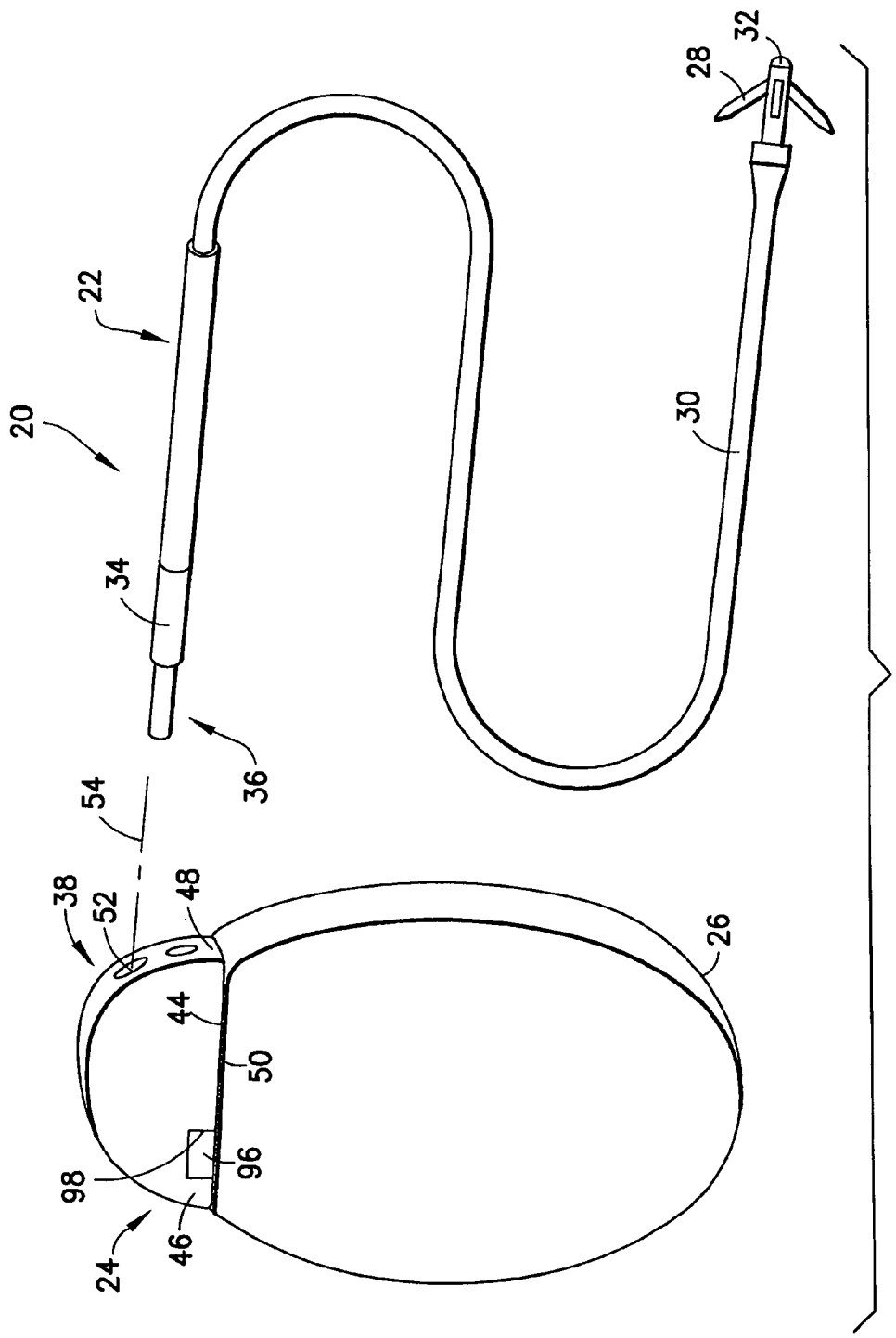
FIG. 1 is a perspective view illustrating of a system embodying the invention including an implantable lead in combination with a stimulating medical device or pulse generator such as a pacemaker.

Refer now to the drawings and, initially, to FIG. 1 which illustrates a diagrammatic perspective view of a system 20 for coupling a body implantable medical electrical lead 22 to a medical device or pulse generator 24 including a sealed housing or casing 26 containing electronic circuitry for delivering electrical stimuli to body tissue. The lead 22 is of the endocardial type which may be attached to an interior wall of a heart by means of fixing tines 28, for example, which engage the tissue or trabeculae of the heart. The lead 22 also includes an insulating sheath 30 interconnecting a distal electrode 32 secured adjacent the interior wall of the heart, for example, and an electrical connector 34 at a proximal end 36 for attachment to the medical device or pulse generator 24, such as a pacemaker. The terms medical device, pulse generator, and pacemaker may be used interchangeably in this disclosure and the term pacemaker is not intended to be restrictive of the type of pulse generator to which the invention has application. Attachment of the electrical connector 34 to the pulse generator 24 is achieved via a connector assembly, or header, 38 incorporating features of the present invention. Although the present invention will be described with reference to the embodiments shown in the drawings, it should be understood that the present invention can be embodied in many alternate forms or embodiments. In addition, any suitable size, shape or type of elements or materials could be used.

Figure 2:
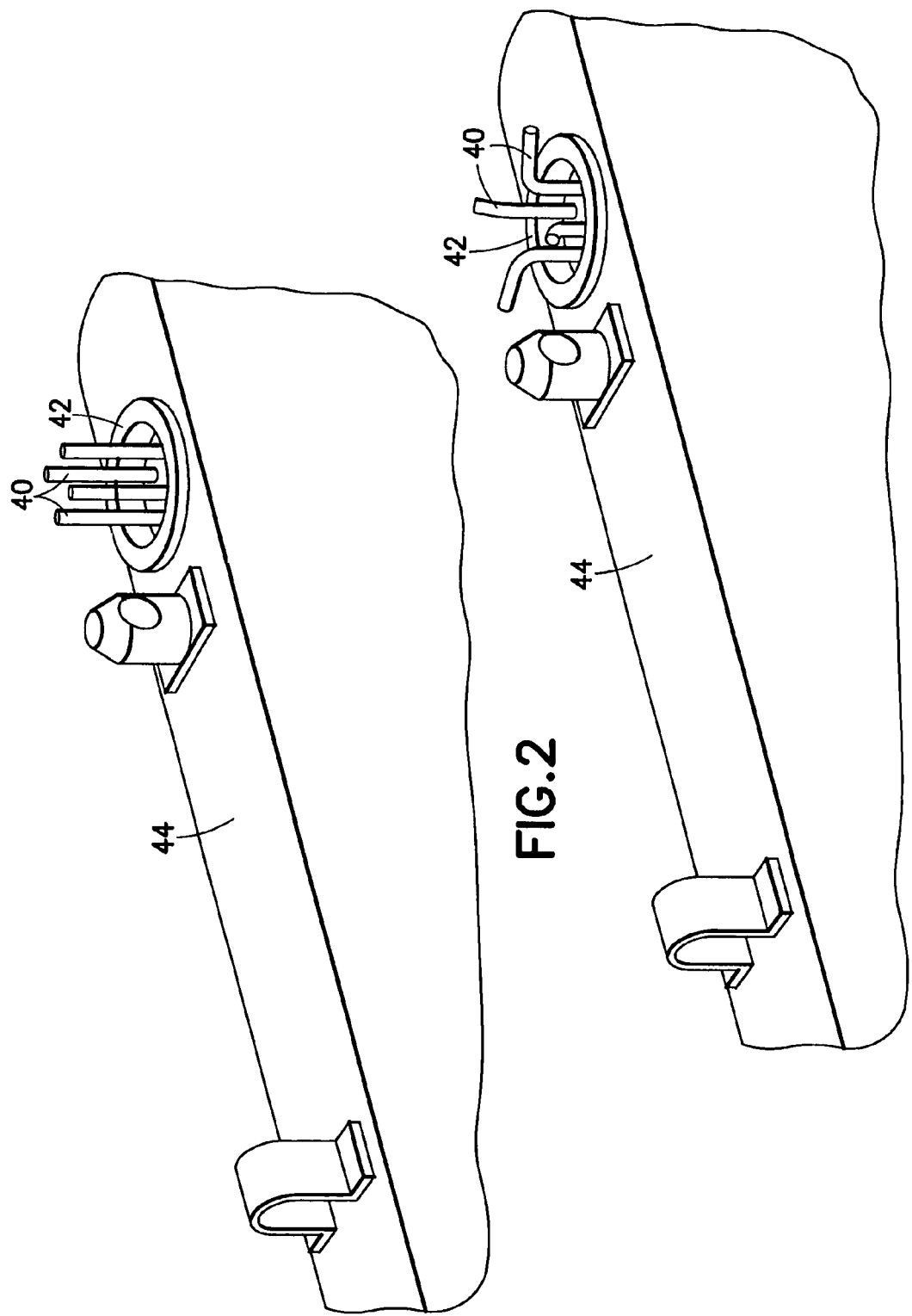
FIG. 2 is a perspective view illustrating a portion of the casing of the medical device illustrated in FIG. 1.
Figure 3:
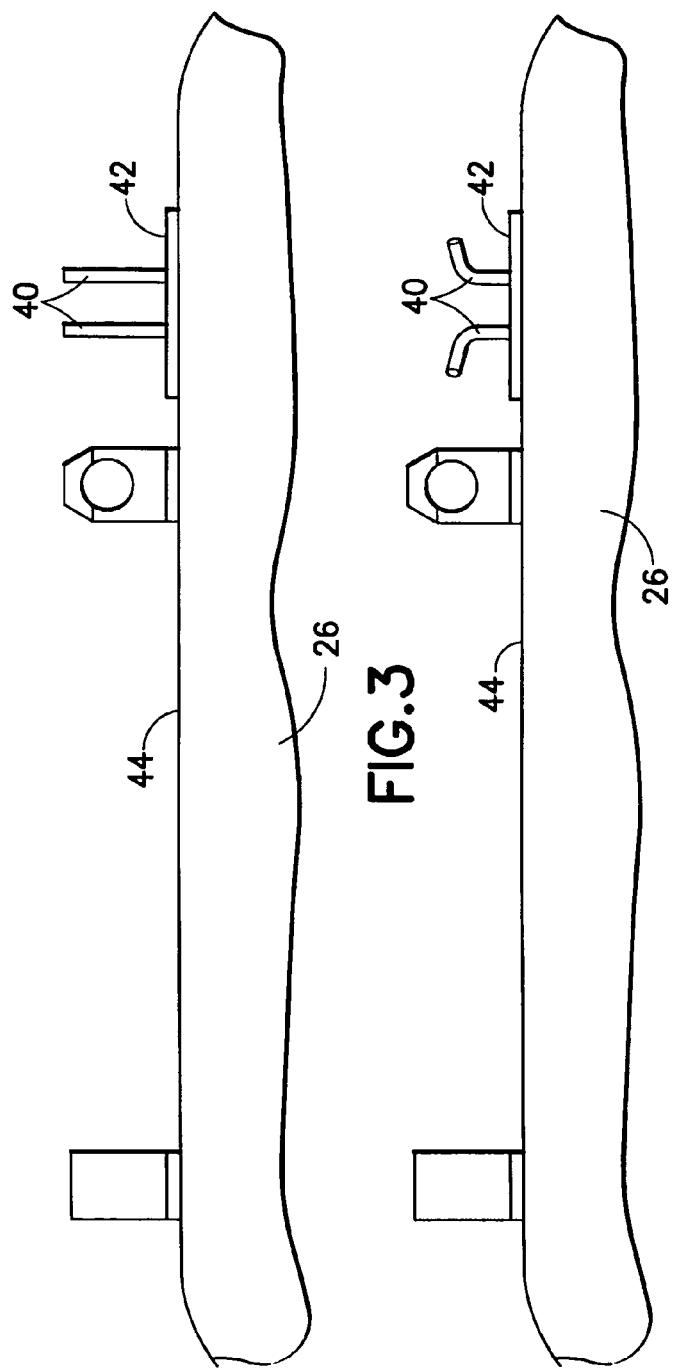
FIG. 3 is a side elevation view of the casing of the medical device illustrated in FIG. 2.
Figure 4:
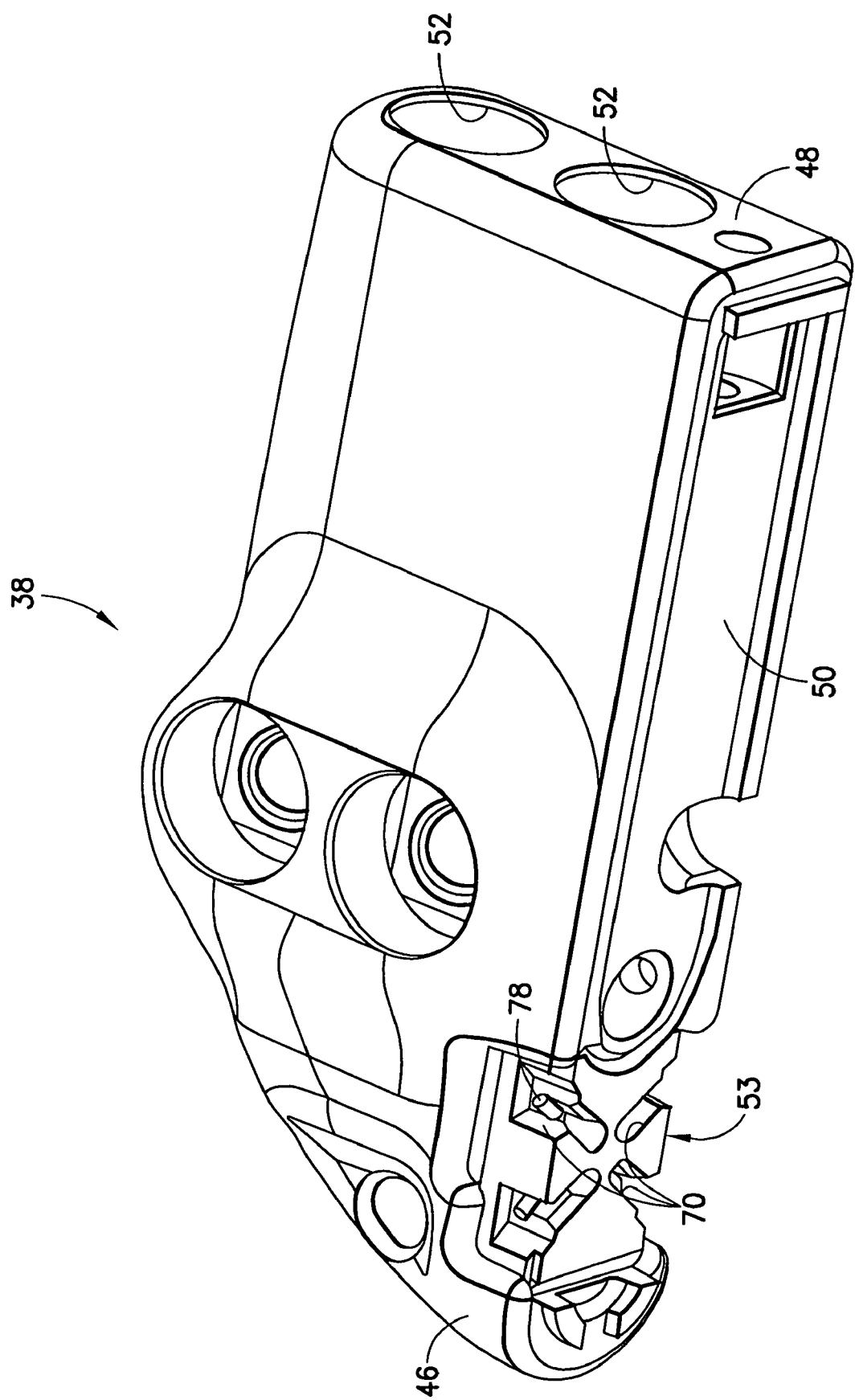
FIG. 4 is a perspective view illustrating the header of the medical device illustrated in FIG. 1.
Figure 5:
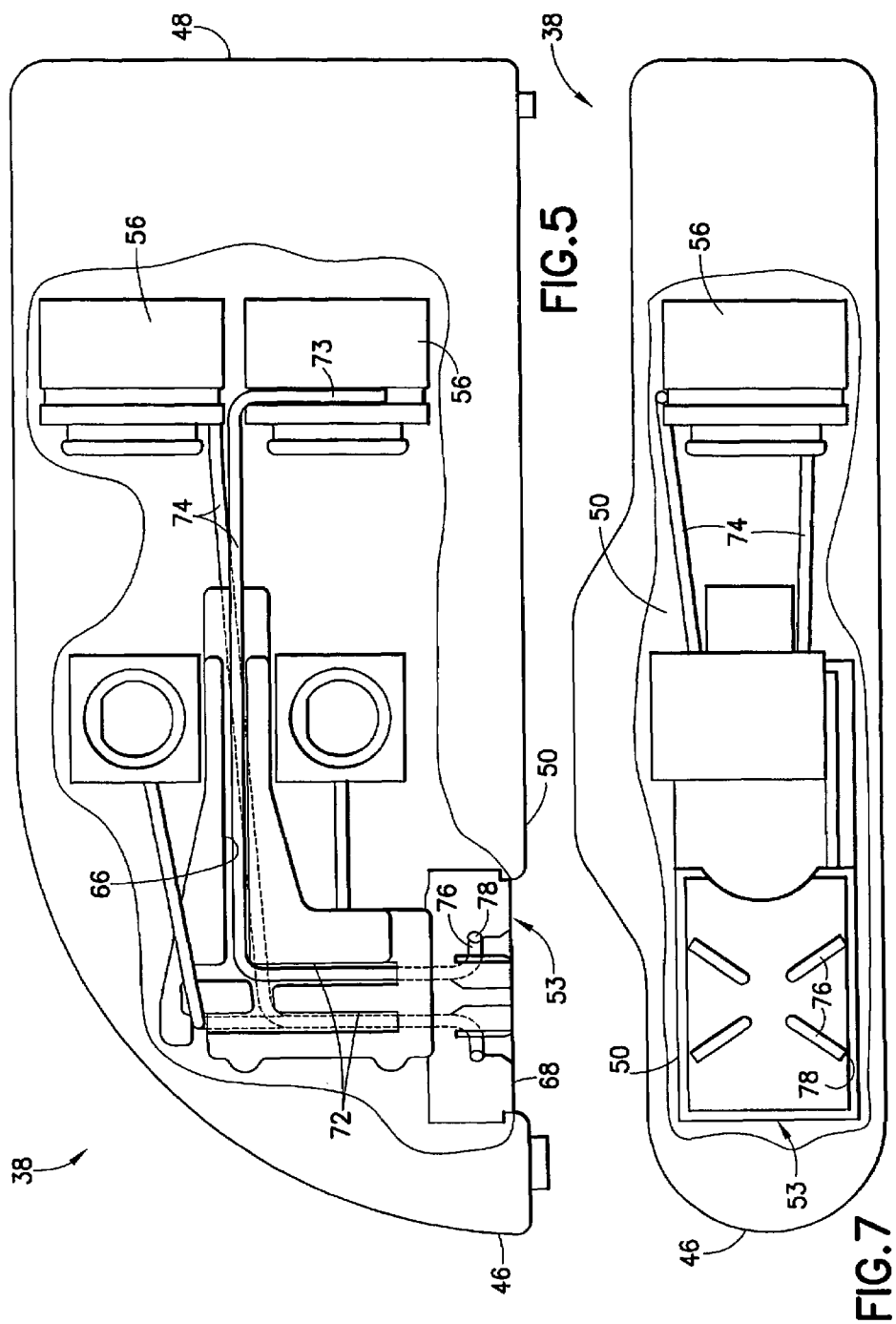
FIG. 5 is a side elevation view of the header with certain portions being broken away to illustrate the interior thereof.
Figure 6:
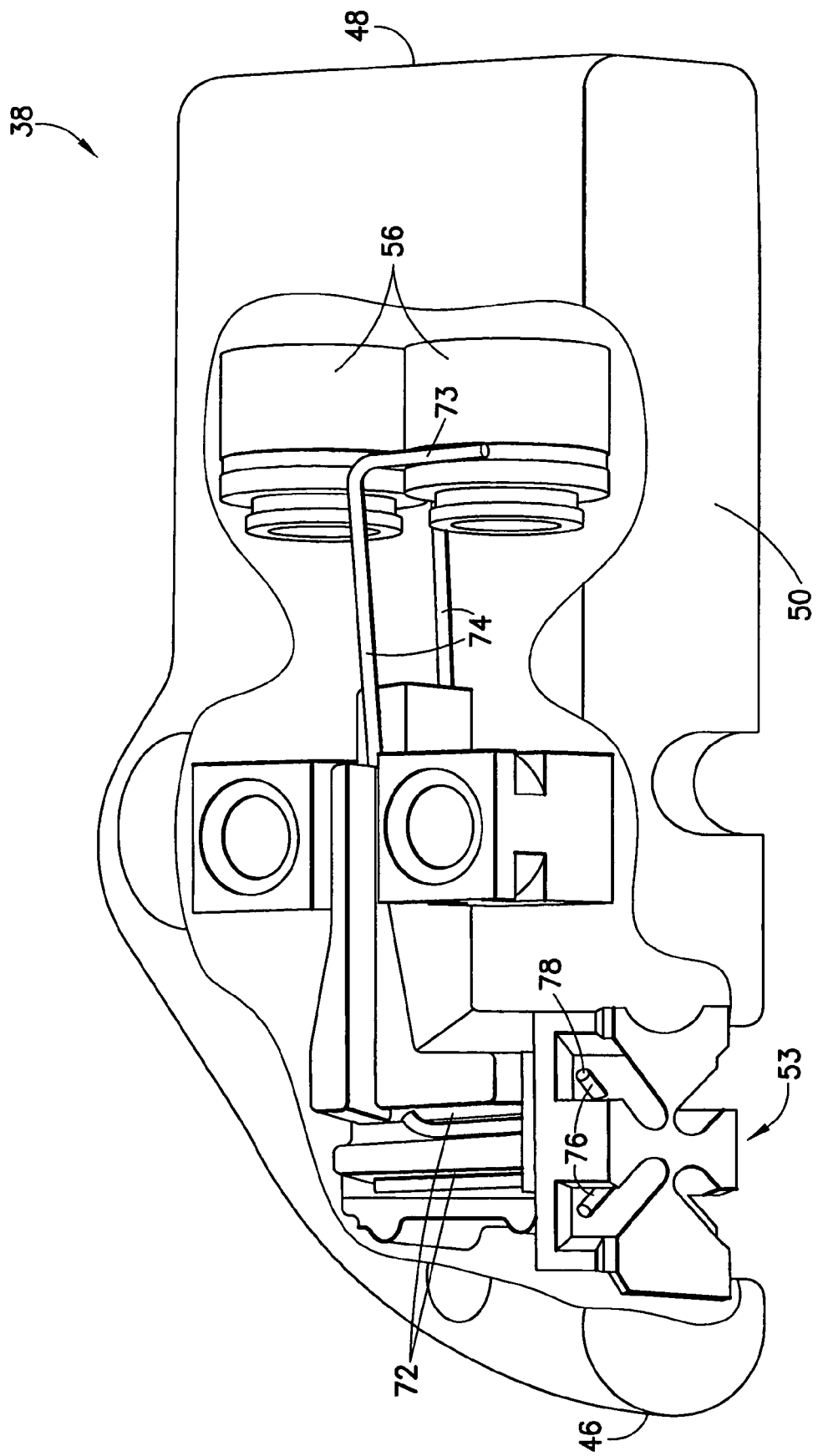
FIG. 6 is a perspective view of the header with certain portions being broken away to illustrate the interior thereof.
Figure 8:
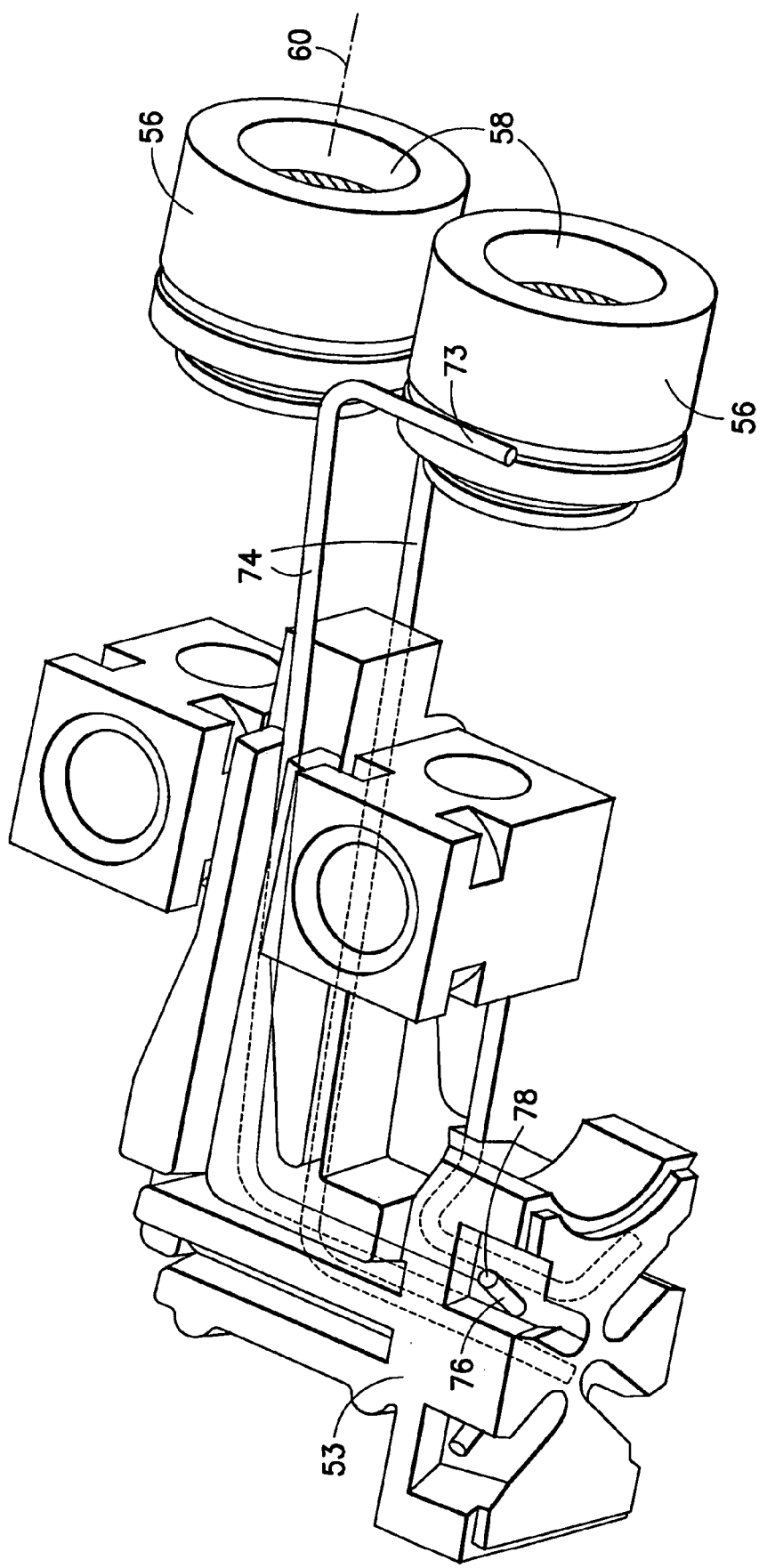
FIG. 8 is a perspective view of certain isolated components which are located within the header.
Figure 9:
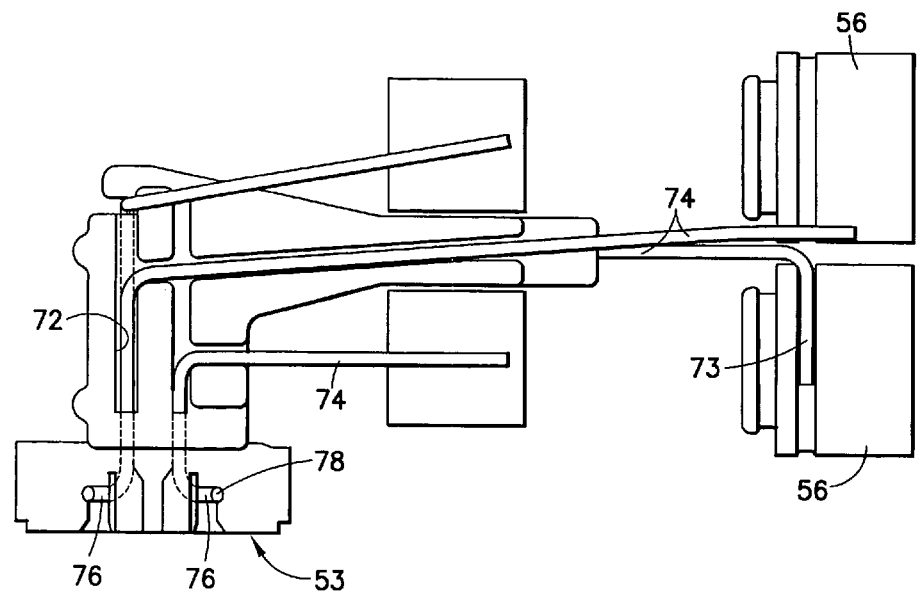
FIG. 9 is a side elevation view of the isolated components illustrated in FIG. 8.

As can be seen in FIGS. 2 and 3, a plurality of feedthru wires 40 connected to the electronic circuitry within the casing 26 project through a feedthru 42 in a mounting surface 44 of the casing. The header 38 is seen extending between proximal and distal ends 46, 48, respectively, and has an undersurface 50 for mounting engagement on the mounting surface 44 of the casing 26. The header contains a plurality (two illustrated) of generally parallel elongated receptacles 52, each aligned with a longitudinal axis 54. Additionally, viewing FIGS. 4-9, the header 38 includes a plurality of electrically conductive connector blocks 56. Each connector block 56 has a bore 58 (FIG. 8) with a longitudinal axis 60 aligned with the longitudinal axis 54 of its associated receptacle 52 for receiving the proximal end portion 36 of the lead 22 extending through its associated receptacle 52 and carrying the electrical connector 34. The receptacles 52 are configured, as needed, to receive the proximal end portions 36 of pacing and/or sensing leads of cardioverting and/or defibrillating leads.

Figure 10:
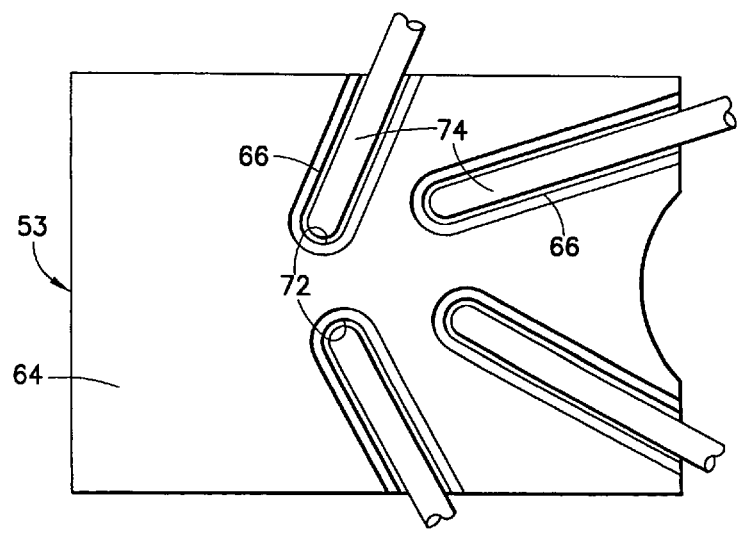
FIG. 10 is a detail top plan view of a portion of the isolated components illustrated in FIGS. 8 and 9.

A feedthru adapter 53 has a top surface 64 (FIG. 10) with a plurality of first chamfered orientation channels 66 formed thereon, an undersurface 68 with a plurality of second chamfered orientation channels 70 having a predetermined azimuthal direction formed therein, and a hole 72 extending from the top surface to the undersurface.

Figure 11:
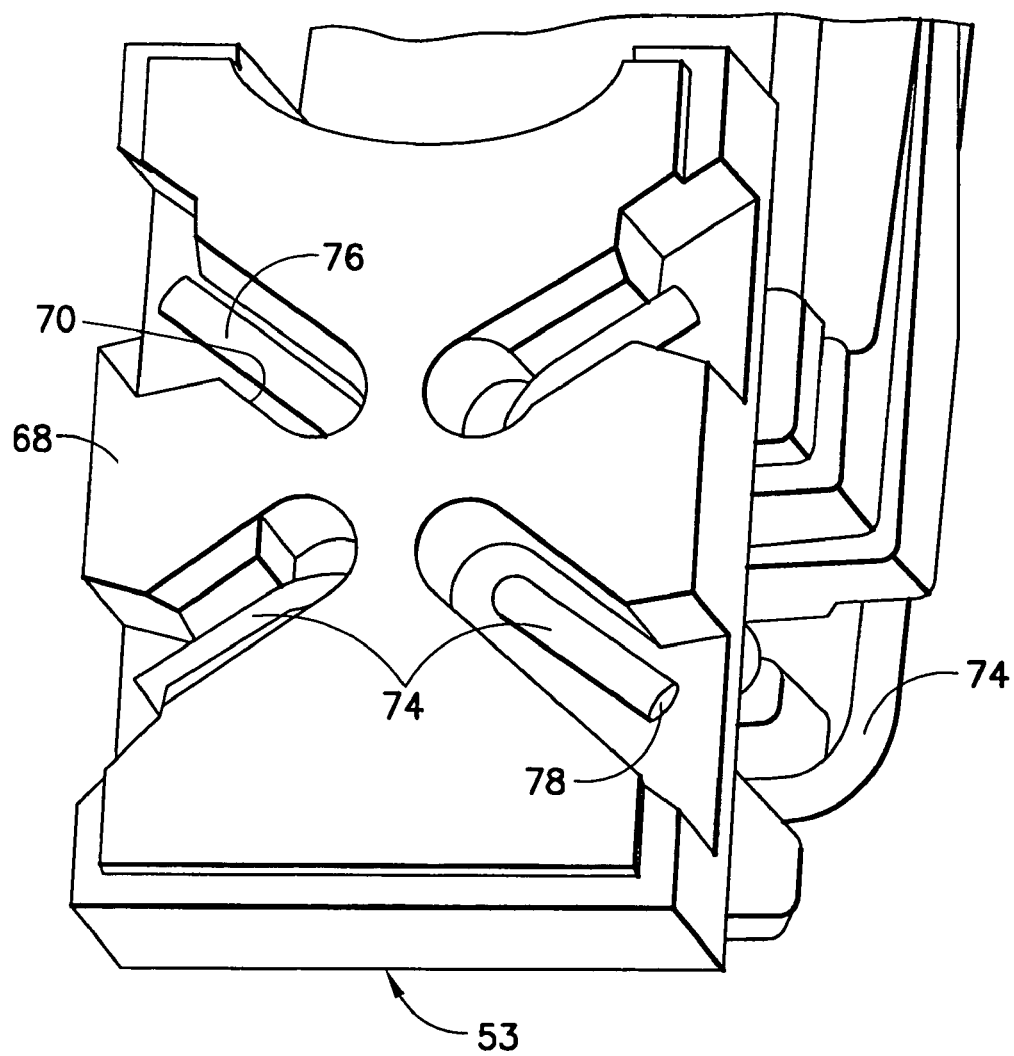
FIG. 11 is a detail perspective view, from beneath, of a portion of the isolated components illustrated in FIGS. 8 and 9.

One end 73 of a bore contact wire 74 is attached to each connector block 56 and a length of each bore contact wire distant from the one end is keyed with an associated first orientation channel 66 passing through the hole 72 including an end portion 76 (FIG. 11) extending to a tip end 78 and bent into conformance with an associated second orientation channel 70 formed on the undersurface 68 of the feedthru adapter 53.

The header 38 is of suitable plastic or composite insulative material. It may be premolded, preferably injection molded. The header 38 encapsulates the feedthru adapter 53, the connector blocks 56, and the bore contact wires 74 and, as earlier noted, has an undersurface 50 for mounting engagement on the mounting surface 44 of the casing 26. It was also earlier mentioned that the header 38 is formed with elongated receptacles 52 with longitudinal axes 54 aligned with associated longitudinal axes 60 of the bores 58 of the connector blocks 56, each receptacle positioned to receive the proximal end portion 36 of the lead 22 as it engages the connector block 56. The header 38 is mounted to the casing 26 so its undersurface 50 is in engagement with the mounting surface 44 of the casing.

Viewing FIGS. 12A, 12B, 12C, and 12D, a fixture device 80, which may be of one or two pieces, has a profiled undersurface 82 conformably engageable with the mounting surface 44 of the casing 26 when removably positioned thereon and has an opening 84 through which the feedthru wires 40 project and has an upper surface 86 formed with a plurality of orientation channels 88. Each orientation channel 88 lies in a plane generally parallel with the mounting surface 44 of the casing 26 when the fixture device is positioned on the mounting surface. With the fixture device 80 so positioned on the casing 26, each feedthru wire 40 is bent at a location of the intersection of the opening 84 with the upper surface 86 so that the feedthru wire lies in engagement with its associated orientation channel 88. Preferably, the fixture device 80 has a pair of trimming channels 90 in the upper surface 86 which extend transverse of the orientation channels 88. With this construction, an end portion of each feedthru wire 40 adjacent its tip end can be trimmed so that a new tip end 94 is formed at the trimming channel so as to be coextensive with its associated orientation channel 88, that is, so that the feedthru wire corresponds to the length of the orientation channel. The end result may be seen in FIGS. 2A, 3A, and 3B.

Figure 13:
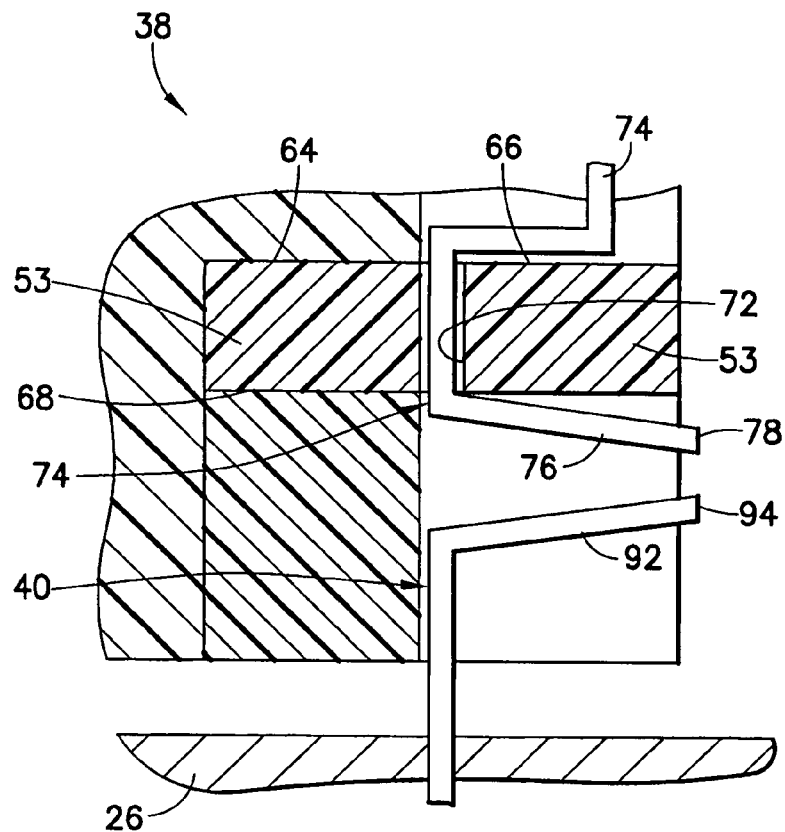
FIG. 13 is a detail side elevation view, in section, illustrating the mounting of the header on the casing of the medical device.
Figure 14:
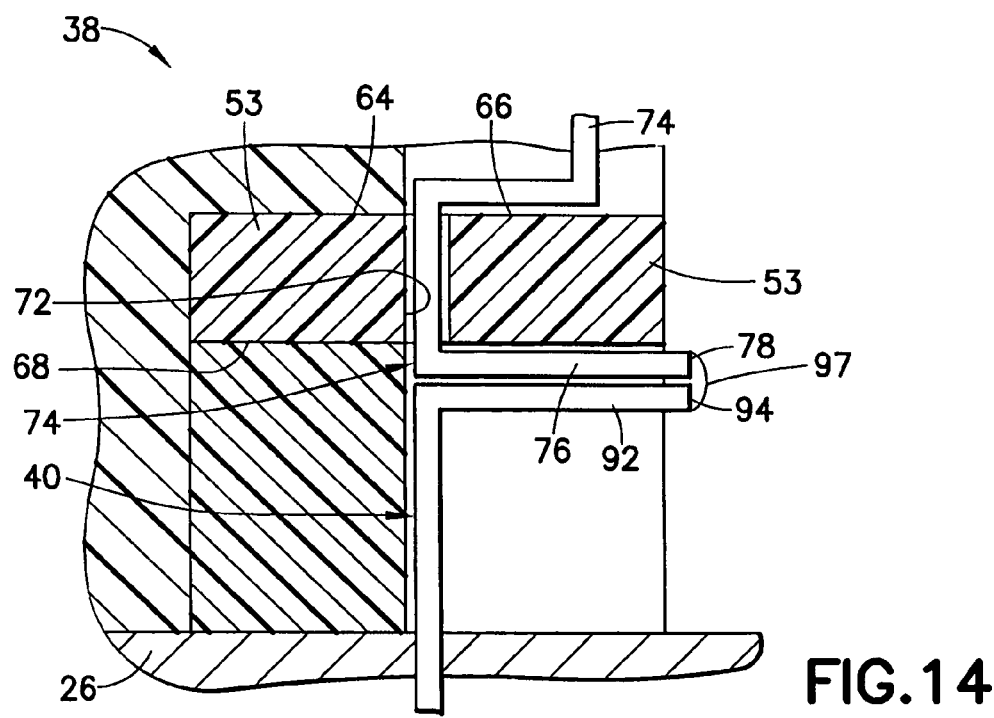
FIG. 14 is a detail side elevation view, in section, similar to FIG. 13 illustrating a later step in the mounting of the header on the casing of the medical device.

After the trimming operation for the feedthru wires 40, and a similar trimming operation may be performed for the bore contact wires 74, viewing FIG. 13, an end portion 92 of each feedthru wire 40 extends to the new tip end 94 in a direction generally aligned with the predetermined azimuthal direction of an associated second orientation channel 70 on the underside of the feedthru adapter 53. As the header is advanced toward the casing 26 so the under surface 50 is brought into engagement with the mounting surface 44, the end portions 76 and 92 of the bore contact wires 74 and the feedthru wires 40, respectively, become generally aligned as seen in FIG. 14. In this manner, the tip end 94 of the feedthru wire 40 and the tip end 78 of the bore contact wire 74 terminate in the same direction and lie in substantially the same plane enabling the tip ends 98 and 74 to be welded together, a welded junction being indicated at 97. After the welding operation, sealant material 96 (FIG. 1) is backfilled into an interface 98 between the header 38 and the casing 26.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. A method of making a pre-molded header assembly for an implantable medical device which includes a casing containing electronic circuitry and having a mounting surface and at least one feedthru wire connected to the electronic circuitry and projecting out of the mounting surface, the method comprising the steps of:
   (a) providing an electrically conductive connector block having a bore with a longitudinal axis for engageably receiving a proximal end portion of a lead carrying at least one electrical connector;
   (b) attaching one end of a bore contact wire to the connector block;
   (c) keying a length of the bore contact wire distant from the one end with a guiding channel formed on an upper region of a feedthru adapter and through a transverse channel extending through the feedthru adapter from the upper region to an undersurface thereof;
   (d) continuing to key the bore contact wire by bending an end portion thereof extending to a tip end into conformance with an orientation channel formed on the undersurface of the feedthru adapter and having a predetermined azimuthal direction;
   (e) molding a header encapsulating the feedthru adapter, the connector block, and the bore contact wire which, when solidified, has an undersurface for mounting engagement on the mounting surface of the casing and an elongated receptacle with a longitudinal axis aligned with the longitudinal axis of the bore of the connector block, the receptacle positioned to receive the proximal end portion of the lead as it engages the connector block;
   (f) attaching the molded header to the casing so the undersurface thereof is in engagement with the mounting surface of the casing;
   (g) immediately prior to step (f), bending an end portion of the feedthru wire extending to a tip end in a direction generally aligned with the predetermined azimuthal direction of an associated orientation channel formed on the underside of the feedthru adapter so that the tip end of the feedthru wire and the tip end of the bore contact wire terminate facing in the same direction and lie in the same plane;
   (h) welding together the end portions of the feedthru wire and the bore contact wire; and
   (i) backfilling with sealant material the interface between the header and the casing.

2. The method as set forth in claim 1 wherein the header is of plastic material.

3. The method as set forth in claim 1 wherein step (e) includes the step of:
   (j) injection molding a plastic header.

4. The method as set forth in claim 1 wherein step (g) includes the steps of:
   (j) providing a fixture device having a profiled undersurface conformably engageable with the mounting surface of the casing when removably positioned thereon and having an opening through which the feedthru wire projects and having an upper surface formed with an orientation channel; and
   (k) bending the feedthru wire at a location of the intersection of the opening with the upper surface so that the feedthru wire lies in engagement with the orientation channel.

5. The method as set forth in claim 4 wherein the orientation channel of step (j) lies in a plane generally parallel with the mounting surface of the casing when the fixture device is positioned on the mounting surface.

6. The method as set forth in claim 4 wherein step (g) includes the steps of:
   (l) providing the fixture device with a trimming channel in the upper surface extending transverse of the orientation channel; and
   (m) trimming an end portion of the feedthru wire adjacent the tip end thereof so that a new tip end is formed at the trimming channel.

7. The method as set forth in claim 4 wherein steps (c) and (d) include the steps of:
   (j) providing the feedthru adapter having the upper region with at least the one guiding channel formed therein, the undersurface spaced from the upper region having at least the one orientation channel formed therein, the transverse channel connecting the guiding channel with the orientation channel;
   (k) positioning the bore contact wire to extend through the guiding channel;
   (l) bending the bore contact wire at the intersection of the upper region with the transverse channel and directing it through the transverse channel toward the undersurface;
   (m) at the intersection of the transverse channel with the undersurface, bending the bore contact wire and positioning the bore contact wire to extend through the orientation channel;
   (n) trimming an end portion of the bore contact wire adjacent the tip end so that a new tip end is formed corresponding to the length of the orientation channel and the feedthru wire;
   (o) forming the orientation channel so as to be generally aligned with the orientation channel of the fixture device; and Including the step, before step (e) of:
   (p) removing the fixture device from the casing.

* * * * *